United States Patent
Horlitz et al.

(10) Patent No.: US 10,233,508 B2
(45) Date of Patent: Mar. 19, 2019

(54) VIRUS PARTICLE STABILISATION AND METHOD FOR ISOLATING VIRAL NUCLEIC ACIDS

(71) Applicant: QIAGEN GmbH, Hilden (DE)

(72) Inventors: Martin Horlitz, Hilden (DE); Markus Sprenger-Haussels, Hilden (DE); Annabelle Schubert, Hilden (DE); Uwe Oelmüller, Hilden (DE)

(73) Assignee: QIAGEN GmbH, Hilden (DE)

( * ) Notice: Subject to any disclaimer, the term of this patent is extended or adjusted under 35 U.S.C. 154(b) by 0 days.

(21) Appl. No.: 14/422,979

(22) PCT Filed: Aug. 21, 2013

(86) PCT No.: PCT/EP2013/067352
§ 371 (c)(1),
(2) Date: Feb. 20, 2015

(87) PCT Pub. No.: WO2014/029792
PCT Pub. Date: Feb. 27, 2014

(65) Prior Publication Data
US 2015/0240320 A1    Aug. 27, 2015

(30) Foreign Application Priority Data
Aug. 21, 2012 (EP) .................................. 12181135

(51) Int. Cl.
| | |
|---|---|
| A61K 39/00 | (2006.01) |
| C07K 14/00 | (2006.01) |
| C07K 14/765 | (2006.01) |
| A61K 38/00 | (2006.01) |
| C07K 14/76 | (2006.01) |
| C12Q 1/70 | (2006.01) |
| C12N 7/00 | (2006.01) |
| C12N 7/02 | (2006.01) |
| C12N 15/10 | (2006.01) |

(52) U.S. Cl.
CPC ............... *C12Q 1/70* (2013.01); *C12N 7/00* (2013.01); *C12N 7/02* (2013.01); *C12N 15/1003* (2013.01)

(58) Field of Classification Search
CPC .... A61K 48/00; A61K 38/00; C12N 15/1003; C12N 15/67; C12Q 11/6806
See application file for complete search history.

(56) References Cited

U.S. PATENT DOCUMENTS

| | | | |
|---|---|---|---|
| 5,459,073 A | 10/1995 | Ryan | |
| 5,460,797 A | 10/1995 | Ryan | |
| 6,255,477 B1 | 7/2001 | Kleiber et al. | |
| 6,617,170 B2 | 9/2003 | Augello et al. | |
| 7,270,953 B2 | 9/2007 | Holländer et al. | |
| 8,304,187 B2 * | 11/2012 | Fernando ............. | C12Q 1/6806 435/6.1 |
| 2005/0059054 A1 | 3/2005 | Conrad et al. | |
| 2009/0023205 A1 | 1/2009 | Dennig et al. | |
| 2009/0048439 A1 | 2/2009 | Weisburg et al. | |
| 2009/0081678 A1 | 3/2009 | Ryan et al. | |
| 2009/0123988 A1 | 5/2009 | Holländer et al. | |
| 2010/0129794 A1 | 5/2010 | Fabis et al. | |
| 2010/0209930 A1 * | 8/2010 | Fernando ............. | C12Q 1/6806 435/6.16 |
| 2011/0111410 A1 | 5/2011 | Ryan et al. | |

FOREIGN PATENT DOCUMENTS

| | | |
|---|---|---|
| DE | 10 2005 040 259 A1 | 3/2007 |
| DE | 10 2005 058 979 A1 | 6/2007 |
| EP | 0 343 934 A2 | 11/1989 |
| EP | 0 880 537 B1 | 12/1998 |
| EP | 1 108 743 A2 | 6/2001 |
| EP | 1 260 595 A2 | 11/2002 |
| EP | 2 395 082 A1 | 12/2011 |
| WO | 95/21849 A1 | 8/1995 |
| WO | 96/41811 A1 | 12/1996 |
| WO | 98/31461 A1 | 7/1998 |
| WO | 98/31840 A1 | 7/1998 |
| WO | 01/71732 A2 | 9/2001 |
| WO | 03/004150 A1 | 1/2003 |
| WO | 2004/003231 A2 | 1/2004 |
| WO | 2006/077020 A2 | 7/2006 |
| WO | 2011/057184 A1 | 5/2011 |
| WO | 2012/007581 A1 | 1/2012 |
| WO | 2014/029791 A1 | 2/2014 |

OTHER PUBLICATIONS

QIAmp MinElute Virus Spin Kit, 2006, XP002688193: pdf pp. 1-3.*
Baechler et al., "Expression levels for many genes in human peripheral blood cells are highly sensitive to ex vivo incubation," *Genes and Immunity* 5:347-353 (2004).
Genov et al., "Stability of subtilisins and related proteinases (subtilases)," *International Journal of Peptide & Protein Research* 45:391-400 (1995).
Günther et al., "Implementation of a proficiency testing for the assessment of the preanalytical phase of blood samples used for RNA based analysis," *Clinica Chimica Acta* 413:779-786 (2012).
Kruhøffer et al., "Isolation of Microarray-Grade Total RNA, MicroRNA, and DNA from a Single PAXgene Blood RNA Tube," *Journal of Molecular Diagnostics* 9(4):452-458 (2007).
Qiagen: "QIAamp MinElute Virus Spin Kit," Oct. 26, 2006, XP002688193, Retrieved from the Internet: URL:http://www.qiagen.com/products/rnastabilizationpurification/cellviralrnapurificationsystems/qiaampmineluteviruspin.aspx? printerFriendly=true (3 pages) [retrieved on Nov. 28, 2012].
Pahl et al., "Gene expression changes in blood after phlebotomy: implications for gene expression profiling," *Blood* 100(3) (2 pages) (2002).

(Continued)

*Primary Examiner* — Barry A Chestnut
(74) *Attorney, Agent, or Firm* — Seed IP Law Group LLP (57) ABSTRACT

The present disclosure provides methods, compositions and devices for isolating virus particles and/or viral nucleic acids from body samples that were stabilized using a stabilizing composition comprising a formaldehyde releaser agent.

18 Claims, 1 Drawing Sheet

(56) References Cited

OTHER PUBLICATIONS

Rainen et al., "Stabilization of mRNA Expression in Whole Blood Samples," *Clinical Chemistry* 48(11):1883-1890 (2002).

Sakudo et al., "Efficient capture of infectious H5 avian influenza virus utilizing magnetic beads coated with anionic polymer," *Biochemical and Biophysical Research Communications* 377:85-88 (2008).
Sakudo et al., "Anionic polymer, poly(methyl vinyl ether-maleic anhydride)-coated beads-based capture of human influenza A and B virus," *Bioorganic & Medicinal Chemistry* 17:752-757 (2009).
Sakudo et al., "Use of anionic polymer, poly(methyl vinyl ether-maleic anhydride)-coated beads for capture of respiratory syncytial virus," *Bioorganic & Medicinal Chemistry Letters* 19:4488-4491 (2009).
Sakudo et al., "Capture of infectious borna disease virus using anionic polymer-coated magnetic beads," *Neuroscience Letters* 494:237-239 (2011).

* cited by examiner

VIRUS PARTICLE STABILISATION AND METHOD FOR ISOLATING VIRAL NUCLEIC ACIDS

The work leading to this invention has received funding from the European Community's Seventh Framework Programme (FP7/2007-2013) under grant agreement n° 222916.

FIELD OF THE INVENTION

The technology disclosed herein relates to methods for isolating virus particles and/or viral nucleic acids from a biological sample obtained from a body, in particular a body fluid such as a blood sample and methods for stabilisation.

BACKGROUND

Human infection by viruses is one of the major health problems facing the mankind. For example, about 180 million people worldwide are infected with hepatitis C virus (HCV). Although an array of pharmaceutical drugs are available now, the use of these drugs requires the monitoring of the efficacy of the drugs by measuring the virus concentration in blood samples, commonly known as the viral load. The viral load is normally determined by measuring the viral nucleic acid concentration in the blood samples (serum or plasma). A number of methods have been developed for measuring viral nucleic acid concentration with the most commonly used method being amplification methods, such as the polymerase chain reaction (PCR).

The most cumbersome step to carry out a PCR is the isolation of viral nucleic acid from the sample, particularly for those samples with very low viral concentration. For the detection of low viral load, the samples are often centrifuged to enrich the viruses using an ultracentrifugation process, which requires an expensive ultracentrifuge and a long centrifugation time. An alternative method for enriching viral particles is binding the virus particles to a solid phase. Thereby, the virus particles are enriched from the original sample.

The viral nucleic acids can then be isolated from the virus particle enriched fraction. Thereby, advantageously, a concentration of the viral particles from large sample volumes is possible.

However, the amount and recoverability of available virus particles and the corresponding viral nucleic acids can decrease substantially over a period of time due to degradation. Thus, the virus load decreases over time, thereby potentially falsifying the results. However, a successful medical treatment of infectious diseases like HCV depends largely on the reliable and accurate quantification of the viral load and hence the viral nucleic acids in patient samples. But clinics where blood collection takes place and laboratories performing viral level determination are often physically separated. Delivering samples from clinics to laboratories often takes place under unfavourable conditions like temperature variations, mechanical shocks and delay resulting in a decrease of viral level loads. In order to stabilize the viral nucleic acid levels in whole blood samples through shipment a blood collection tube containing a stabilizing reagent is required.

Blood samples containing virus particles are usually collected in blood collection tubes containing spray-dried or liquid EDTA as anticoagulant (e.g. BD Vacutainer $K_2$EDTA). EDTA chelates magnesium, calcium and other bivalent metal ions, thereby inhibiting enzymatic reactions, such as e.g. blood clotting or DNA degradation due to DNases. However, EDTA does not stabilize virus particles which usually consist of two or three parts: the genetic material made from either DNA or RNA, long molecules that carry genetic information; a protein coat that protects these genes; and in some embodiments an envelope of lipids that surrounds the protein coat when they are outside a cell. Thus, viruses as well as viral nucleic acids are susceptible to degradation.

Thus, it is inter alia an object of the present invention to provide a method for stabilizing virus particles in a biological sample, in particular a sample obtained from a human body, and to provide a suitable method for isolating virus particles and/or viral nucleic acids from a stabilized sample.

SUMMARY OF THE INVENTION

The present invention is based on the finding that the isolation of virus particles and/or viral nucleic acids from stabilized samples can be significantly improved if the sample is stabilized with a stabilization composition comprising one or more formaldehyde releaser agents. Thereby, virus particles are effectively stabilized even over prolonged time. This efficient stabilization of the virus particles improves not only the subsequent isolation of the virus particles if a separate isolation of the virus particles is desired, but is also advantageous when aiming at isolating viral nucleic acids from the sample, e.g. in order to determine the virus load in a biological sample obtained from a human body, in particular in order to determine the virus load in a body fluid such as blood or a sample derived therefrom.

Therefore, in a first aspect the present disclosure relates to a method for isolating virus particles and/or viral nucleic acids from a biological sample obtained from a body, also referred to herein as "body sample", comprising the steps of:
 a) obtaining a stabilized body sample, wherein said sample was stabilized by contacting the sample with a stabilization composition comprising at least one formaldehyde releaser agent to stabilize virus particles and viral nucleic acids comprised in the sample; and
 b) isolating virus particles and/or viral nucleic acids from the stabilized sample or from a portion, fraction or component of the stabilized body sample.

The formaldehyde releaser agent based stabilization according to the present disclosure has the effect that virus particles and also viral nucleic acids contained in a body sample such as a body fluid sample are substantially preserved in the state they have shown at the time the body sample was obtained, respectively was collected. The substantial preservation of the virus particles and the viral nucleic acids is an important advantage because this stabilization/preservation enhances the accuracy of any subsequent tests that aim at detecting and/or quantifying the virus particles and/or viral nucleic acids. This stabilization allows for standardizing the isolation and subsequent analysis and/or quantification of the virus particles and/or viral nucleic acids, thereby making diagnostic or prognostic applications that are based on the quantitative or qualitative detection of virus particles and/or viral nucleic acids more reliable and more independent from the used storage/handling conditions. It is an advantage of the methods according to the present disclosure that after the isolation of the virus particles and/or the viral nucleic acids a reliable and accurate quantification of the virus particles and/or viral nucleic acids comprised in a body sample is possible. This is important for a successful diagnosis and/or medical treatment of a virus based infectious disease. By substantially preserving the virus particles and viral nucleic acids at the time the sample was collected, the diagnostic and prognostic applicability of the respectively isolated virus particles and/or viral nucleic acids is improved. The stabilizing composition as disclosed herein is particularly effective in stabilizing a body sample, in particular whole blood, plasma,serum and/or bone marrow aspirates, and in particular stabilizes the virus particles and the viral nucleic acids comprised in said body sample, thereby improving the isolation of viral nucleic acids from the body sample.

According to a further aspect, the present disclosure pertains to a method for stabilizing viral particles in a body sample or in a sample obtained therefrom, wherein said method comprises a step of contacting the sample with a stabilization composition comprising at least one formaldehyde releaser.

According to a further aspect, the present disclosure pertains to a method for the identification, quantification or monitoring of a virus disease, comprising performing the isolation method according to the first aspect of the present disclosure, wherein the isolated virus particles and/or isolated viral nucleic acids are analyzed (e.g., by quantity, quality, or both) for the presence, absence, or severity of a virus disease and/or for disease monitoring purposes.

According to a further aspect, the present disclosure pertains to the use of a biological sample collection container, in particular an evacuated collection container, for stabilizing viral particles in a biological sample obtained from a body, preferably a body fluid, wherein the container comprises a stabilization composition comprising a formaldehyde releaser agent. Using a respective container, e.g. a sample collection tube comprising the stabilizing composition, has the advantage that the body sample and viral particles potentially comprised therein is immediately stabilized as soon as the sample is collected in the respective container.

Other objects, features, advantages and aspects of the present application will become apparent to those skilled in the art from the following description and appended claims. It should be understood, however, that the following description, appended claims, and specific examples, while indicating preferred embodiments of the application, are given by way of illustration only. Various changes and modifications within the spirit and scope of the disclosed invention will become readily apparent to those skilled in the art from reading the following.

DETAILED DESCRIPTION OF THE INVENTION

The present disclosure is directed to technologies that are suitable for stabilizing virus particles and viral nucleic acids in a biological sample obtained from a body (also referred to herein as body sample), preferably a human body, such as in particular a blood sample, thereby improving the subsequent isolation of viral particles and/or viral nucleic acids from the stabilized sample. Thereby, the detection and quantification of virus particles and/or viral nucleic acids is improved what is important in the medical and diagnostic field. The achieved improvements with respect to the efficient isolation of viral nucleic acids from the stabilized body samples are inter alia based on the efficient stabilization of the viral particles comprised in the body sample. The efficient stabilization of the virus particles and the viral nucleic acids allows the storage and the handling of the stabilized samples for a prolonged period of time at room temperature without jeopardizing the quality of the sample. As the composition of the viral nucleic acids comprised in the body sample is stabilized and thus substantially preserved at the time the sample is obtained by using the teachings of the present disclosure, the time between sample collection and virus particle isolation and/or nucleic acid isolation can vary without significant effect on the virus particles and/or the viral nucleic acids. This allows the standardization of e.g. diagnostic virus infection analysis because variations in the handling/storage of the samples have less influence on the quality, respectively the viral loads of the body samples, thereby providing an important advantage over prior art methods.

According to a first aspect, a method for isolating virus particles and/or viral nucleic acids from a body sample is provided, said method comprising the steps of:
 a) obtaining a stabilized body sample, wherein said sample was stabilized by contacting the sample with a stabilization composition comprising at least one formaldehyde releaser agent to stabilize virus particles and viral nucleic acids comprised in the sample; and
 b) isolating virus particles and/or viral nucleic acids from the stabilized sample or from a portion, fraction or component of the stabilized sample.

The terms "virus," "viruses", "virus particle" and "virus particles" are and can be used interchangeably, and include all viruses (e.g., enveloped and non-enveloped) which carry proteins on their surface, including envelope proteins, coat proteins and cellular membrane proteins, as well as "naked viruses" which lack such surface proteins. Respective naked viruses may be e.g. modified to include surface proteins (e.g., by insertion of the proteins into the outer lipid bilayer of the virus). Viruses include for example, but are not limited to, retroviruses and DNA viruses. The term "virus particle" as used herein refers to the fully or partially assembled capsid of a virus. A viral particle may or may not contain nucleic acid; preferably it comprises nucleic acids. Virus particles according to the present disclosure may consist of two or three parts: the genetic material made from either DNA or RNA, long molecules that carry genetic information; a protein coat that protects the genetic material; and in some embodiments an envelope of lipids that surrounds the protein coat when they are outside a cell. In body samples, such as e.g. blood, plasma, semen, vaginal fluid, pre-ejaculate and breast milk, viruses can be present within infected cells and/or as free virus particles. Methods for isolating viral particles from body samples are known and include e.g. nanofiltration as well as virus particle isolation procedures wherein the virus particles are bound to a solid phase. Embodiments are described subsequently.

The genomes of the virus particles may be single-stranded (ss) or double-stranded (ds), RNA or DNA, circular or linear, structured in singular or multiple nucleic acid molecules/fragments per virus particle, and may or may not use reverse transcriptase (RT). Additionally, ssRNA viruses may be either sense (+) or antisense (−). According to the present disclosure, the virus particles may be viruses selected from the group consisting of dsDNA viruses (e.g. Adenoviruses, Herpesviruses, Poxviruses), ssDNA viruses (+)sense DNA (e.g. Parvoviruses), dsRNA viruses (e.g. Reoviruses), (+)ss- RNA viruses (+)sense RNA (e.g. Picornaviruses, Togaviruses), (−)ssRNA viruses (−)sense RNA (e.g. Orthomyxoviruses, Rhabdoviruses), ssRNA-RT viruses (+)sense RNA with DNA intermediate in life-cycle (e.g. Retroviruses) and dsDNA-RT viruses (e.g. Hepadnaviruses).

Virus particles include both RNA and DNA viruses and include but are not limited to Human Papillomaviruses, Hepatitis Viruses, including Hepatitis A, Hepatitis B and Hepatitis C virus, Human Immunodeficiency Virus, Herpes Viruses, including Herpes Simplex Viruses, Epstein-Barr-Viruses, Cytomegaloviruses and Varicella Zoster Viruses, Astroviruses, Caliciviruses, Coronaviruses, Picornaviruses, Coxsackieviruses, Human Echoviruses and Paraechoviruses, Kaposi's sarcoma-associated Herpesvirus, Polyomavirus, e.g. Merkel cell polyomavirus, human T-lymphotropic virus, Adenoviruses, Rhinoviruses, Enteroviruses, Influenza Viruses, Parainfluenza Viruses, Human Metapneumovirueses, Polioviruses, Human Respiratory Syntycial Virus, Dengue Viruses, Parvoviruses and Paramyxoviruses. In some embodiments, the virus particles cause cancer in humans and other species. In some embodiments, human papillomaviruses that cause cancers of cervix, skin, anus, and penis are stabilized in the method according to the present invention.

The terms "viral nucleic acids" or "viral nucleic acid" as used herein, can be used interchangeably and in particular refer to nucleic acids from viruses as mentioned above. In advantageous embodiments, the viral nucleic acids are derived from the virus particles contained in the stabilized sample.

The body sample from which the virus particles and/or viral nucleic acids may be isolated include any body sample comprising or suspected of comprising a virus or any sample obtained from a respective body sample. Preferably, the body sample is obtained from a human, in particular a human patient. Biological samples obtained from a body, also referred to herein as "body samples" or "body sample", include but are not limited to body fluids and tissues. The body sample can be selected from the group consisting of whole blood, bone marrow aspirates, lymphatic fluid, urine, liquor, ascites, milk, saliva, amniotic fluid, semen/seminal fluid, bronchoalveolar lavages, body secretions, nasal secretions, vaginal secretions, wound secretions or samples obtained from the aforementioned body fluids, such as e.g. plasma or serum samples that are obtained from blood. In advantageous embodiments, the body sample is a body fluid and preferably is selected from whole blood, plasma, serum and urine, and more preferably the body sample is whole blood.

Subsequently, we will explain the individual steps and preferred embodiments of the present invention:

First, a stabilized sample is obtained, wherein the sample stabilization involved the use of at least one formaldehyde releaser. Respectively stabilized samples may be obtained, e.g. received from a facility wherein the sample was collected, such as e.g. a hospital. However, the stabilization and nucleic acid isolation may also be performed at the same facility. Thus, the method according to the present invention may also comprise a step of collecting and stabilizing the sample using the stabilization described herein. The sample is stabilized upon collection by contacting the sample with a stabilization composition comprising at least one formaldehyde releaser agent. The stabilisation method that is used according to the present invention has important advantages because it substantially maintains the integrity of the virus particles and/or viral nucleic acids comprised in the sample. This improves the subsequent isolation of the virus particles and/or viral nucleic acids.

The sample stabilization involves the use of a stabilizing composition which comprises one or more formaldehyde releaser. A formaldehyde releaser as used herein is a compound which over time releases formaldehyde and/or paraformaldehyde. Thus, formaldehyde and/or paraformaldehyde are slowly released. The formaldehyde releaser acts as preservative agent. The formaldehyde releaser may be a chemical fixative. Suitable formaldehyde releasers include but are not limited to, diazolidinyl urea, imidazolidinyl urea, dimethoylol-5,5dimethylhydantoin, dimethylol urea, 2-bromo-2.-nitropropane-1,3-diol, oxazolidines, sodium hydroxymethyl glycinate, 5-hydroxymethoxymethyl-1-1 aza-3,7-dioxabicyclo[3.3.0]octane, 5-hydroxymethyl-1-1 aza-3,7dioxabicyclo[3.3.0]octane, 5-hydroxypoly[methyleneoxy]methyl-1-1 aza-3,7dioxabicyclo[3.3.0]octane, quaternary adamantine or any combinations of the foregoing. The formaldehyde releaser preferably is a heterocyclic urea and may be selected from the group consisting of diazolidinyl urea (DU), imidazolidinyl urea (IDU), and any combination thereof. In advantageous embodiments, the stabilization involved the use of diazolidinyl urea (DU) and/or imidazolidinyl urea, preferably diazolidinyl urea.

The use of a formaldehyde releaser to stabilize a sample has compared to typical histological fixing agents such as e.g. formaldehyde the advantage that the toxicity is very low. It is thus preferred that the stabilizing composition is non-toxic and preferably free of separately added formaldehyde and/or separately added paraformaldehyde. According to one embodiment, the whole stabilization of the sample did not involve the addition of formaldehyde or paraformaldehyde as chemical compounds. According to one embodiment, the stabilization of the sample did not involve the use of an additional fixative which cross-links proteins.

The formaldehyde releaser can be used alone for stabilization purposes. However, depending on the type of sample and also the intended storage time, further additives may be contained in the stabilization composition or may be added separately to the sample to be stabilized in order to improve the stabilization effect. For example, when stabilizing blood or a sample derived from blood, the stabilization will involve the addition of an anticoagulant.

Examples of anticoagulants that can be comprised in the stabilization composition or can be added separately to the sample for stabilization include but are not limited to heparin, metal ion chelating agents, in particular citrate, oxalate, EDTA and combinations thereof. These and other anticoagulants are also well-known in the prior art. However, in order to achieve an immediate stabilization and to directly prevent the lysis of the contained cells it is preferred that the anticoagulant and the stabilization composition are either given at or approximately at the same time or, preferably, to include the anticoagulant in the stabilization composition which comprises the formaldehyde releaser.

Further suitable additives that may be added either separately to the sample or may form part of the stabilization composition are described in the following. These are of course non-limiting and accordingly, other additives may be included respectively may be added as well.

According to one embodiment, the stabilization composition that was used for stabilizing the sample or the stabilization process as such may have further comprised the use of one or more additional additives. Said one or more additives may be selected from the group consisting of enzyme inhibitors, preferably nuclease inhibitors, more preferably RNase inhibitors, metabolic inhibitors, preferably glyceraldehyde, cell membrane permeabilisers, amino acids, protease inhibitors, phosphatase inhibitors, oxidative stress neutralizers such as e.g. antioxidants or reactive oxygen species and metal ion chelators. Preferably, two or more of the respective additives are comprised in the stabilization composition or are added separately during the stabilization process. Suitable examples are described below. Therein, we specifically refer to the embodiment, wherein the one or more optional additives are provided as constituent of the stabilization composition. However, as described above, these one or more optional additives may also be added separately for stabilization. Thus, the subsequent disclosure equally applies to embodiments, wherein said optional additives are added separately from the formaldehyde releaser.

In advantageous embodiments, the stabilization composition that was used to provide the stabilized sample comprised one or more enzyme inhibitors like nuclease inhibitors in a suitable amount to prevent DNase and/or RNase activity from decreasing the quality and amount of nucleic acids recoverable from the sample. Nuclease inhibitors that may be used for stabilization include, but are not limited to diethyl pyrocarbonate, ethanol, aurintricarboxylic acid (ATA), formamide, vanadyl-ribonucleoside complexes, macaloid, ethylenediamine tetraacetic acid (EDTA), proteinase K, heparin, hydroxylamine-oxygen-cupric ion, bentonite, ammonium sulfate, dithiothreitol (DTT) 1 beta-mercaptoethanol, cysteine, dithioerythritol, tris(2-carboxyethyl) phosphene hydrochloride, or a divalent cation such as $Mg^{+2}$, $Mn^{+2}$, $Zn^{+2}$, $Fe^{+2}$, $Ca^{+2}$, $Cu^{+2}$ and any combination thereof.

Preferred nuclease inhibitors inactivate nucleases (e.g. RNases) by binding to them so that the nucleases are no longer capable of contacting the nucleic acids comprised in the sample thereby reducing the adverse effects of nucleases on the quantity and quality of the nucleic acids. In an advantageous embodiment, the nuclease inhibitors used for stabilization include aurintricarboxylic acid (ATA) and/or metal ion complexing agents such as ethylenediamine tetraacetic acid (EDTA).

The stabilization composition used for stabilizing the sample may have also included one or more metabolic inhibitors in a suitable amount to reduce cell metabolism within a body sample which preferably is a body fluid sample. Metabolic inhibitors that may be used include, but are not limited to glyceraldehyde, dihydroxyacetone phosphate, glyceraldehyde 3-phosphate, 1,3-bisphosphoglycerate, 3-phosphoglycerate, 2-phosphoglycerate, phosphoenolpyruvate, pyruvate and glycerate dihydroxyacetate, sodium fluoride, $K_2C_2O_4$ and any combination thereof. In advantageous embodiments, the metabolic inhibitor is sodium fluoride and/or glyceraldehyde.

The stabilization composition may have also included one or more metal ion chelators in a suitable amount, wherein the metal ion chelator is selected from the group consisting of ethylene glycol tetraacetic acid (EGTA), 1,2-bis-(o-Aminophenoxy)-ethane-N',N',-N',N'-tetraacetic acid tetraacetoxy-Methyl ester (BAPTA-AM), dietyldithiocarbamate (DEDTC), ethylenediaminetetraacetic acid (EDTA), dicarboxymethyl-glutamic acid, nitrilotriacetic acid (NTA), ethylenediaminedisuccinic acid (EDDS), polycarboxylic acids, citrate and any combination thereof. In advantageous embodiments, the metal ion chelator is EDTA. As described above, metal ion chelators may function as nuclease inhibitors. Furthermore, and this is particularly advantageous when stabilizing a blood sample or a sample derived from blood, metal ion chelators can function as anticoagulant. The metal ion chelator is preferably comprised in a concentration so that it acts as anticoagulant, in particular if the sample is a blood sample.

Preferably, the stabilization composition is an aqueous composition, preferably an aqueous solution. The stabilization composition that was used for providing the stabilized sample may have comprised suitable solvents such as water, buffers (e.g. MOPS, TRIS, PBS and the like), saline, dimethylsulfoxide, alcohol and any mixture thereof. According to one embodiment, the stabilization composition used is a solution which comprises/has comprised a heterocyclic urea such as diazolidinyl urea and/or imidazolidinyl urea in a buffered salt solution. The stabilization composition which preferably is a solution may have further comprised an anticoagulant, preferably EDTA and optionally ATA. The stabilization composition solution may also comprise/have comprised one or more metabolic inhibitors, preferably sodium fluoride and/or glyceraldehyde and/or a nuclease inhibitor.

It is within the scope of the present invention that the stabilization composition that was used for stabilisation is not in a liquid but in a solid form. For example, all or selected components of the stabilization composition may undergo a lyophilisation process so that each component is added either prior to or post collection in a substantially solid form. This may help e.g. to prevent unwanted reactions between one or more components of the stabilization composition. Liquid removal techniques can be performed on the stabilization composition in order to obtain a substantially solid state stabilization composition. Liquid removal conditions may preferably be such that they result in removal of at least about 50 percent by weight, more preferable about 75 percent by weight, and still more preferably at least about 85 percent by weight of the original amount of the dispensed liquid stabilization composition. Liquid removal conditions may preferably be such that they result in removing of sufficient liquid so that the resulting composition is in the form of a film, gel or other substantial solid or highly viscous layer, for example it may result in a substantially immobile coating (preferably a coating that can be re-dissolved or otherwise dispersed upon contact with the sample to be stabilized). Thus, liquid removal conditions may preferably be such that they result in a material that upon contact with the sample under consideration the stabilization composition in its constituents will disperse in the sample, and substantially preserve the components in the sample, such as in particular the cells and contained nucleic acids. Liquid removal conditions may preferably be such that they result in a remaining composition that is substantially free of crystallinity, has a viscosity that is sufficiently high and that the remaining composition is substantially immobile at ambient temperature. Respective liquid removal techniques are well known to the skilled person and thus, do not need a detailed description here.

The amount of any active ingredient within the stabilization composition and in particular the amount of formaldehyde releaser necessary to achieve a sufficient stabilization of a specific sample may vary from sample to sample and in particular depends on the characteristics of the sample, in particular the amount of the comprised cells. Suitable concentrations can be determined by skilled person and only require routine experiments. Suitable concentration ranges for liquid stabilization compositions are given in the following. These compositions are particularly suitable for stabilising body fluids such as blood. Any percentages given by weight refer in case of a liquid composition to weight per volume.

The amount of any active ingredient within the stabilization composition may generally be at least about 0.01 percent by weight. The amount of any active ingredient within the stabilization composition may generally be 90 percent by weight or less, 85 percent by weight or less, 80 percent by weight or less, 75 percent by weight or less, 70 percent by weight or less, 60 percent by weight or less, 50 percent by weight or less or 40 percent by weight or less. The stabilization composition may comprise at least about 10 percent by weight, preferably at least about 15 percent by weight, more preferred at least 20 percent by weight formaldehyde releaser, which preferably is diazolidinyl urea. The stabilization composition may comprise 90 percent by weight or less, 85 percent by weight or less, 80 percent by weight or less, 75 percent by weight or less, 70 percent by weight or less, 65 percent by weight or less, 60 percent by weight or less, 55 percent by weight or less, 50 percent by weight or less, 45 percent by weight or less or 40 percent by weight or less formaldehyde releaser which preferably is diazolidinyl urea. The stabilization composition may further contain at least about 0.1 percent by weight, at least 0.5 percent by weight or at least 1 percent by weight of one or more enzyme inhibitors (e.g., nuclease inhibitors) such as EDTA and ATA. The stabilization composition may contain less than about 40 percent by weight or less than about 30 percent by weight of one or more enzyme inhibitors, such as a nuclease inhibitor. The stabilization composition may also contain at least about 1 percent by weight, preferably at least about 2 percent by weight of one or more metabolic inhibitors. The stabilization composition may contain 40 percent by weight or less, 30 percent by weight or less, 20 percent by weight or less, 15 percent by weight or less, or 10 percent by weight or less of one or more metabolic inhibitors. Preferably, glyceraldehyde is used as metabolic inhibitor.

In advantageous embodiments, the stabilization composition that was used for providing the stabilized sample comprises a formaldehyde releaser in a concentration selected from 10 to 70 percent by weight, 10 to 60 percent by weight or 10-50 percent by weight, preferably 15 to 40 percent by weight, more preferred 20-30 percent by weight. Preferably, diazolidinyl urea and/or imidazolidinyl urea is used as formaldehyde releaser. In another advantageous embodiment the stabilization composition comprises in addition to the formaldehyde releaser an enzyme inhibitor in a concentration selected from 0.05 to 40 percent by weight, 0.1 to 30 percent by weight, 0.1 to 20 percent by weight, 0.1 to 10 percent by weight or 0.1 to 5 percent by weight, preferably 0.5 to 3 percent by weight, more preferred 0.5-2.5 percent by weight. In one embodiment ATA is used as enzyme inhibitor. In a further advantageous embodiment the stabilization composition comprises in addition to the formaldehyde releaser and optionally in addition to the enzyme inhibitor at least one metabolic inhibitor in a concentration selected from 0.05 to 40 percent by weight, 0.05 to 30 percent by weight, 0.05 to 20 percent by weight, 0.05 to 15 percent by weight, 0.05 to 12.5 percent by weight or 0.05 and 8 percent by weight, preferably glyceraldehyde in a concentration selected from 1-8 percent by weight and/or sodium fluoride in a concentration selected from 0.05-1.5 percent by weight. In other advantageous embodiments the stabilization composition comprises in addition to the formaldehyde releaser and optionally in addition to the enzyme inhibitor and/or the metabolic inhibitor a metal ion chelator in a concentration selected from 0.1 to 40 percent by weight, 1 to 30 percent by weight, 2.5 to 25 percent by weight, 5 percent to 20 percent by weight, preferably 5-15 percent by weight.

In embodiments according to the present disclosure, the stabilization composition that was used for providing the stabilized sample comprises
  a) a formaldehyde releaser selected from a chemical fixative that contains urea, preferably diazolidinyl urea and/or imidazolidinyl urea,
and in addition thereto, at least one, preferably at least two, preferably all of the following components:
  b) an enzyme inhibitor, preferably aurintricarboxylic acid,
  c) a metabolic inhibitor, preferably glyceraldehyde and/or sodium fluoride, and/or
  d) a metal ion chelator, preferably EDTA.

Suitable and preferred concentration ranges for the respective components were described above. Said stabilization composition is when comprising an anticoagulant, such as a metal ion chelator, particularly suitable for stabilizing body fluids, in particular whole blood samples or samples derived from blood.

The stabilization composition is contacted with the sample for stabilization. The amount of stabilization composition to be added to the sample to achieve stabilization depends on the type of sample, the intended storage time and the storage temperature. According to one embodiment, the stabilization composition is mixed with the sample in a ratio selected from 1:1000 to 1000:1, 1:100 to 100:1, 1:75 to 75:1, 1:60 to 60:1, 1:50 to 50:1, 1:40 to 40:1, 1:30 to 30:1, 1:25 to 25:1, 1:20 to 20:1, 1:15 to 15:1, 1:10 to 10:1, 1:5 to 5:1, 1:3 to 3:1, 1:2 to 2:1 and 1:1. It is an advantage that already a small amount of the stabilization composition is sufficient to stabilize even difficult samples such as whole blood or blood products. E.g. a ratio of 1:50 (e.g. 200 µl stabilization composition mixed with 10 ml blood) is sufficient to stabilize whole blood samples. Thus, according to one embodiment, the stabilization composition is contacted with the sample, which preferably is a body fluid, more preferred blood or a sample derived from blood, in a ratio selected from the following ranges 1:75 to 1:1, preferably 1:60 to 1:5, more preferred 1:50 to 1:10.

Samples that were stabilized as described above may be kept e.g. stored without refrigeration, preferably at room temperature, for a time period of at least one day, at least two days, at least three days, at least one day to at least three three days, or selected from at least one day to at least seven days and/or at least one day to at least fourteen days (two weeks). Good stabilization effects were observed even at prolonged storage periods.

As is described above and as is demonstrated by the examples, using the methods of the present invention allows for stabilizing the sample, preferably a body fluid, without refrigeration or freezing for a prolonged period of time. Thus, the samples can be kept at room temperature or even at elevated temperatures e.g. up to 30° C. or up to 40° C. According to one embodiment, a stabilization effect is achieved for at least two days, preferably at least three days; more preferred at least one day to at least six days, most preferred for at least one day to at least seven days at room temperature. As is shown in the examples, the samples that were stabilized according to the method of the present disclosure were not substantially compromised when stored for 3 days at room temperature. Even during longer storages for up to 5 or even 7 days at room temperature the viral nucleic acids were substantially more stabilized compared to non-stabilized samples or e.g. compared to samples that were stabilized using standard method such as an EDTA treatment. As spiking experiments with virus particles were performed, the examples also demonstrate the stabilization of the virus particles contained in the body sample. Even though the stabilization effect may decrease over time, it is still sufficient to preserve the composition of the viral nucleic acids to allow the subsequent analysis and/or further processing. Thus, samples that were stabilized according to the methods of the present disclosure were still suitable for isolating and optionally analysing the virus particles and/or the viral nucleic acids contained therein even after longer storage at room temperature. Thus, as the samples were not compromised in particular when using the preferred combination of additives, even longer storage/shipping times are conceivable. Therefore, the samples stabilized according to the present teachings were even after longer storage periods suitable for determining the viral load. However, usually, longer periods are not necessary, as the regular storage and e.g. shipping time to the laboratory, wherein the nucleic acid isolation and optionally analysis is performed, usually does not exceed 5 or 7 days, but usually is even completed after two or three days. As is shown in the examples, the stabilisation efficiency is particularly good during this time period.

The stabilization technology that is used according to the present invention is of particular advantage because it substantially preserves the viral load and in particular the virus particles and/or the viral nucleic acids in the sample and e.g. inhibits degradation of the viral load. Preferably, degradation of the viral load is reduced by at least 40%, at least by 50%, at least by 60%, at least by 70% or at least by 75% over the stabilization period compared to an unstabilized sample or an EDTA stabilized sample. Preferably, the degradation is reduced by at least 1.5-fold, preferably at least 2-fold, more preferably is reduced by at least 2.5-fold.

The stabilizing composition described above and/or the stabilization additives if provided separately can be e.g. present in a device for collecting the sample, which preferably is a body fluid sample, or can be added to a respective collection device immediately prior to collection of the sample or can be added to the collection device preferably immediately after the sample was collected therein. Preferably, the collection device is a blood collection device. Preferably, said collection device is an evacuated collection container, such as a tube. It is also within the scope of the present invention to add the formaldehyde releaser agent(s) and optionally, the further additive(s) separately to the virus particle containing body sample, respectively the body sample suspected of containing virus particles. However, for the ease of handling, it is preferred that the one or more of the additives are provided in the collection device, preferably in form of one stabilization composition. Furthermore, in an advantageous embodiment, a formaldehyde releaser agent and optionally the further additives such as an enzyme inhibitor, a metabolic inhibitor and/or a metal ion chelator are present in a collection device prior to adding the sample. This ensures that the virus particles containing body sample, respectively the body sample that is suspected of containing respective virus particles, is immediately stabilized upon contact with the stabilizing composition. The stabilizing composition is present in the container in an amount effective to provide the stabilization of the amount of sample, preferably body fluid sample, to be collected, respectively comprised in said container. Also disclosed herein is a virus particle containing body sample, preferably a body fluid such as blood, stabilized as described herein comprised in a sample collection device.

The stabilization of the body sample may be followed directly by processing techniques for analyzing the viral particles and/or viral nucleic acids or the stabilized sample can be stored or shipped before the stabilized sample is further processed. E.g. the virus particles and/or the viral nucleic acid can be isolated from the stabilized body sample or from a fraction, portion or component of the stabilized sample and can then be analysed in a nucleic acid analytic and/or detection method or may be further processed in another suitable way.

As discussed above, the stabilization according to the present disclosure has the effect that the virus particles and/or the viral nucleic acids and hence the viral load contained in the body sample, which preferably is a body fluid such as blood, is substantially preserved in the state it had shown at the time the sample was obtained, respectively drawn. Virus particles and/or viral nucleic acids are then isolated in a further step from the stabilized sample, of from a portion, fraction or component of the stabilized sample. Several options exist how the obtained stabilized sample can be further processed in order to isolate viral particles and/or viral nucleic acids from the stabilized sample or a portion, fraction or component thereof or for determining the viral load of the stabilized sample. According to one embodiment, the viral particles and/or the viral nucleic acids are only isolated from a portion, fraction or component of the stabilized sample. According to one embodiment, said portion, fraction or component comprises or predominantly consists of cells. E.g. cells in general or a specific cell type may be isolated from the stabilized sample and the viral nucleic acids are subsequently isolated from the obtained cells. However, according to a preferred embodiment, the viral particles and/or the viral nucleic acids are isolated from a cell-depleted or even cell-free portion or fraction of the stabilized body sample which preferably is a body fluid. A preferred embodiment is plasma or serum obtained from a whole blood sample that was stabilized according to the present invention.

According to one embodiment, in step b) virus particles are isolated, e.g. enriched, from the stabilized sample by binding them to a suitable solid phase. Suitable methods for isolating viruses from samples including body fluid samples such as blood or plasma are well-known in the prior art and are e.g. described in EP 1 108 743, WO 2006/077020, WO 2012/007581 Sakudo et al (Bioorganic & Medicinal Chemistry letters 19 (2009) 4488-4491), Sakudo et al (Bioorganic & Medicinal Chemistry letters 17 (2009) 752-757), Sakudo et al (Biochemical and Biophysical Research Communications 377 (2008) 85-88) and Sakudo et al (Neurosciences Letters 494 (2011) 237-239). Respective methods can be used in conjunction with the present invention for isolating viral particles from the stabilized samples. Thus, viral particle isolation methods that can be used in step b) according to the present invention may e.g. use a virus particle binding solid support. Said support may e.g. comprise one or more virus binding entities such as ligands comprising suitable functional groups, which have a binding affinity for the virus particles to be isolated from the stabilized sample. Suitable ligands may comprise anion or cation exchange moieties as is described in the above mentioned prior art methods. The solid support may be provided in form of a column, a membrane, fibers, particles, wells or vessels. The solid support provides a surface, which comprises virus binding entities and thus provides appropriate surface properties for binding the virus particles. The virus binding entities such as ligands may be coupled covalently or non-covalently to the solid support. In certain embodiments, the solid support for isolating the viral particles is provided by magnetic particles. Using magnetic particles as solid support for isolating viral particles has the advantage that the handling is simplified, because the particles can be easily processed by the aid of a magnetic field. Thereby, the magnetic particles to which the viral particles bind, e.g. adsorb, can be easily separated from the remaining sample.

According to one embodiment, a solid support is used which comprises virus binding entities such as a chemical or ligand. Said chemical and/or functional group has affinity for the virus particle to be isolated. The virus binding affinity may be selective. However, solid supports allowing non-selective binding of viral particles can also be used, because the subsequent detection methods such as e.g., polymerase chain reaction (PCR) and antibody-based assays provide the necessary specificity for the target virus. According to one embodiment, the virus binding entity is a pharmaceutical drug that specifically binds the virus surface or a membrane protein thereof, e.g., oseltamivir that binds to neuraminidase of influenza viruses. Other virus binding entities such as ligands comprising functional groups suitable for selectively or non-selectively binding viral particles, e.g. comprising anionic or cationic groups, are also known in the prior art and thus, need no further detailed description here. Furthermore, there are numerous methods available for coupling a virus binding entity to a solid support. These methods are readily available from scientific journals, vendors that provide coupling reagents, or relevant websites. Virus binding ligands and/or functional groups may need to be appropriately modified or derivatized to introduce a functional group that can be used for coupling while at the same time the modification or derivatization does not inactivate the virus binding activity.

Furthermore, the virus binding entities can be chemically or naturally coupled to another moiety that can be subsequently coupled to a solid support. One example is proteins extracted from erythrocyte membrane, which contain glycoproteins with sialic acid; these protein extracts or the specific sugar chains can be coupled to a solid support that can be subsequently used for influenza virus isolation.

The method for virus particle isolation according to step b) may comprise the following steps:

The obtained stabilized body sample, which preferably is a body fluid or bone marrow aspirate, is contacted with a solid support under appropriate conditions (e.g., temperature, incubation duration etc.) to allow binding viral particles to the solid support. The solid support with the bound viral particles is then separated from the remaining sample. For example, if magnetic particles are used as virus particle binding solid support, a magnet can be used to collect the solid support, thereby simplifying the removal of the remaining sample, e.g. the supernatant. The solid support may then be washed one or more times with an appropriate solution such as phosphate-buffered saline (PBS). The respectively isolated virus particles can then be detected, identified or quantified by a number of methods, e.g., by isolating nucleic acids from the enriched viral particles and detection of the target viral nucleic acids, antigen detection, and viral enzyme detection. Thus, according to one embodiment, viral nucleic acids are isolated from the isolated, respectively enriched viral particles using appropriate nucleic acid isolation methods.

According to one embodiment, in step b) viral nucleic acids are isolated from the stabilized sample or portion, fraction or component thereof. Preferably, the viral nucleic acids are isolated from the stabilized sample or from the portion, fraction or component of the stabilized sample without isolating the virus particles first. Preferably, viral nucleic acids are isolated from a cell-depleted or even cell-free fraction of the stabilized sample and preferably are isolated from a plasma sample. The viral nucleic acids may be isolated as part of total nucleic acids, or part of total nucleic acids of one type of nucleic acid (e.g. total RNA or total DNA). The isolation of viral nucleic acids may also comprise the selective isolation of a specific target viral nucleic acid comprised e.g. by using appropriate capture probes that are specific for the viral nucleic acids.

According to one embodiment, substantially all nucleic acid types that are comprised in the stabilized sample or in the portion, fraction or component of the stabilized sample are isolated, e.g. are isolated from the cell-free, respectively cell-depleted fraction of the stabilized sample. E.g. total nucleic acids can be isolated from plasma or serum and the viral nucleic acids will be comprised as a portion in these extracted nucleic acids. It is also within the scope of the present invention to isolate at least predominantly a specific target nucleic acid. A target nucleic acid can be e.g. a certain type of nucleic acid, e.g. RNA or DNA, including mRNA, microRNA, other non-coding nucleic acids, epigenetically modified nucleic acids, and other nucleic acids. It is also within the scope of the present invention to e.g. digest the non-target nucleic acid using nucleases after isolation. The term target nucleic acid also refers to a specific kind of nucleic acid, e.g. a specific viral nucleic acid sequence that is known to be a certain disease marker. As discussed above, the isolation of viral nucleic acids may also comprise the specific isolation of a respective target nucleic acid e.g. by using appropriate capture probes.

Examples of nucleic acid isolation methods that can be used in step b) include but are not limited to nucleic acid extraction, solid-phase extraction, silica-based purification, magnetic particle-based purification, phenol-chloroform extraction, chromatography, anion-exchange based isolation methods (using anion-exchange surfaces), electrophoresis, filtration, precipitation, and combinations thereof. It is also within the scope of the present disclosure to specifically isolate specific target viral nucleic acids, e.g. by using appropriate probes that enable a sequence specific binding and are coupled to a solid support. Also any other nucleic acid isolating technique known by the skilled person can be used that enables the isolation of viral nucleic acids from the stabilized sample or from the portion, fraction or component of the stabilized sample. Preferably, the nucleic acids are isolated by binding them to a solid phase, preferably a solid phase comprising silica or anion exchange functional groups. The nucleic acid isolation method may involve the use of salts such as chaotropic salts or LiCl; respective salt based nucleic acid isolation methods are well-known in the prior art. Suitable methods and kits are also commercially available such as the QIAamp® Circulating Nucleic Acid Kit (QIAGEN), QIAamp MinElute Virus Spin Kit (QIAGEN), QIAamp DSP Virus Kit (QIAGEN), QIAamp Virus BioRobot MDx Kit (QIAGEN), EZ1 DSP Virus Kit (QIAGEN), QIAamp UltraSens Virus Kit (QIAGEN), MagAttract Virus Mini M48 Kit (QIAGEN), QIAsymphony Virus/Pathogen Kit (QIAGEN), QIAsymphony DNA Kit, the Chemagic Circulating NA Kit (Chemagen), the NucleoSpin Plasma XS Kit (Macherey-Nagel), the Plasma/Serum Circulating DNA Purification Kit (Norgen Biotek), the Plasma/Serum Circulating RNA Purification Kit (Norgen Biotek), PerfectPure, the High Pure Viral Nucleic Acid Large Volume Kit (Roche) and other commercially available kits suitable for extracting and purifying viral nucleic acids. Depending on the processed sample, the nucleic acid isolation will often include a lysis step in order to digest the sample and to release the viral nucleic acids from the viral particles. Thus, a lysis step is preferred. However, it is also within the scope of the present invention to directly isolate stabilized viral nucleic acid from the samples, without performing a specific lysis step if the processed sample allows an isolation of the viral nucleic acids without performing a lysis step. The nucleic acid isolation method is automatable and may be performed using a robotic system.

The isolation of viral nucleic acids from a body sample that was stabilized using a formaldehyde releaser agent is potentially challenging because the formaldehyde releaser may disturb the subsequent isolation of viral nucleic acids. A preferred method according to the present invention which allows to efficiently isolate viral nucleic acids from a body sample that was stabilized using at least one formaldehyde releaser involves the following steps:
  a) obtaining a stabilized body sample, preferably a stabilized body fluid sample, wherein the stabilization involved the use of a stabilization composition comprising a formaldehyde releaser agent;
  b) isolating viral nucleic acids from the stabilized body sample or from a portion, fraction or component of the stabilized body sample, wherein the nucleic acid isolation comprises the following steps:
    i) lysing the stabilized body sample or lysing a portion, fraction of component obtained from the stabilized body sample thereby providing a lysed sample;
    ii) providing a binding composition comprising the lysed sample, at least one chaotropic salt and at least one alcohol and binding nucleic acids comprised in the binding composition to a solid phase;
    iii) optionally washing bound nucleic acids;
    iv) optionally eluting bound nucleic acids.

Preferred embodiments of step a) and accordingly stabilization compositions used for obtaining the stabilized sample, stabilization steps and stabilized samples were described above and it is referred to the above disclosure. The stabilized body sample preferably is a stabilized body fluid, more preferred stabilized blood sample. The stabilization composition that was used for stabilizing the body sample, preferably a body fluid such as blood, comprises a formaldehyde releaser agent, preferably in a concentration between 20-30 percent by weight, and may comprise one or more, preferably all, of the following components:
  i) an anticoagulant;
  ii) it comprises an enzyme inhibitor between 0.5-2.5 percent by weight;
  iii) it comprises a metabolic inhibitor between 0.05 and 8 percent by weight, preferably glyceraldehyde between 1-8 percent by weight and/or sodium fluoride between 0.05-1.5 percent by weight;
  iv) it comprises a metal ion chelator between 5-15 vol.-%. percent by weight.

When the body sample stabilized with a formaldehyde releaser agent is blood, the nucleic acids are in step b) preferably isolated from plasma that was obtained from the stabilized blood sample. Plasma is an example of a fraction obtained from a stabilized sample, here a stabilized blood sample. Hence, a step may be performed between step a) and b) for removing cells and optionally further components from the stabilized body sample, which preferably is a stabilized blood sample. The resulting cell-depleted sample corresponds to a portion or fraction of the stabilized sample and is then processed in step b) in order to isolate viral nucleic acids therefrom.

In step b) i., the stabilized body sample or a portion, fraction of component obtained from the stabilized body sample (e.g. plasma or serum) is lysed. The term "lysis" as used herein refers to the disruption, degradation and/or digestion of a sample or portion or fraction thereof. In a respective lysis step, biomolecules such as in particular nucleic acids can be released from cells, viral particles or can be freed from other sample additives such as e.g. proteins. Herein, it is referred to a respective step to disrupt, degrade and/or digest a sample generally as lysis step, irrespective of whether biomolecules such as in particular nucleic acids are released from cells or whether the lysis is performed in order to release biomolecules such as nucleic acids e.g. from virus particles, proteins or other substances comprised in the sample. Hence, the sample may comprise cells or may comprise no or only minor amounts of cells as is e.g. the case with blood plasma. Preferably, for lysis performed in step b) i. the sample is contacted with one or more, preferably all of the following lysing agents:
  aa) a proteolytic enzyme, preferably proteinase K;
  bb) one or more detergents, preferably at least one non-ionic detergent and/or at least one ionic detergent;
  cc) at least one chaotropic agent.

A proteolytic enzyme refers to an enzyme that catalyzes the cleavage of peptide bonds, for example in proteins, polypeptides, oligopeptides and peptides. Exemplary proteolytic enzymes include but are not limited to proteinases and proteases in particular subtilisins, subtilases, alkaline serine proteases and the like. Subtilases are a family of serine proteases, i.e. enzymes with a serine residue in the active side. Subtilisins are bacterial serine protease that has broad substrate specificities. Subtilisins are relatively resistant to denaturation by chaotropic agents, such as urea and guanidine hydrochloride and anionic detergents such as sodium dodecyl sulfate (SDS). Exemplary subtilisins include but are not limited to proteinase K, proteinase R, proteinase T, subtilisin, subtilisin A, QIAGEN Protease and the like. Discussions of subtilases, subtilisins, proteinase K and other proteases may be found, among other places in Genov et al., Int. J. Peptide Protein Res. 45: 391-400, 1995. Preferably, the proteolytic enzyme that is used as lysis supporting agent aa) is proteinase K.

As lysis supporting agent bb) one or more detergents are used. The detergent may be added as part of a composition. Preferably, at least one non-ionic detergent is used which aids the lysis of the sample and which dissolves protein aggregates. Also a mixture of non-ionic surfactants can be used. The non-ionic surfactant preferably is selected from the group consisting of polyoxyethylene fatty alcohol ethers, polyoxyethylene alkylphenyl ethers, polyoxyethylene-polyoxypropylene block copolymers, polysorbates and alkylphenol ethoxylates, preferably polyoxyethylene fatty alcohol ethers, polysorbates and/or polyoxyethylene alkyl phenyl ethers. The term "fatty alcohol" in particular means for the purposes of the present invention alcohols having a chain length of from 6 to 22 carbon atoms, preferably 8 to 20 carbon atoms, preferentially 10 to 18 carbon atoms, particularly preferably 12 to 18 carbon atoms. Preference is in particular given to alcohols having 12, 14, 16 or 18 carbon atoms. Although the fatty alcohols may be mono- or polyunsaturated, they are preferably saturated fatty alcohols. The term "polyoxyethylene" in particular means for the purposes of the present invention an $HO-(CH_2CH_2O)_n$ unit, with n being preferably an integer from 2 to 150, further preferably from 4 to 120, still further preferably from 8 to 80, and most preferably an integer selected from 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 and 50. Preferred examples of suitable polyoxyethylene fatty alcohol ethers are polyethoxylated lauryl, cetyl, oleyl, or stearyl alcohols which may be used alone or as mixture. According to a preferred embodiment of the invention, the at least one polyoxyethylene fatty alcohol ether comprises a fatty alcohol additive having from 6 to 22 carbon atoms and a polyoxyethylene additive having from 2 to 150 ($CH_2CH_2O$) units. Preferably, the polyoxyethylene fatty alcohol ether is selected from the group consisting of polyoxyethylene lauryl ether, polyoxyethylene cetyl ether (Brij-58), polyoxyethylene stearyl ether and/or polyoxyethylene oleyl ether. As alkylglucoside, preferably a nonionic surfactant from the group of the polysorbates, preferably polysorbate 20 (Tween 20), polysorbate 40 or polysorbate 80, more preferred polysorbate 20 is used. Preferred examples of polyoxyethylene alkyl phenyl ethers include Tergitol, Triton X-100 and Nonidet P-40 (nonylphenylpolyethylenglycol). Preferably, a polyoxyethylene fatty alcohol ether, preferably Brij 58 is used as non-ionic detergent. Furthermore, an ionic detergent can be used as lysis supporting agent aa). Said ionic detergent may be anionic and preferably is SDS. According to one embodiment, as lysis supporting agent aa) at least one non-ionic detergent and at least one ionic detergent, preferably at least one anionic detergent, is used.

As lysis supporting agent cc), at least one chaotropic agent, preferably a chaotropic salt, is used. For this purpose a digestion solution can be added which comprises at least one chaotropic agent. Said digestion composition may also comprise additional compounds, in particular the additive bb), and further additives that promote the digestion and/or preserve the comprised nucleic acid. Preferably, the digestion composition is a digestion solution. Any chaotropic agent can be used that causes disorder in a protein or nucleic acid by, for example, but not limited to altering the secondary, tertiary or quaternary structure of a protein or a nucleic acid while leaving the primary structure intact. Preferred chaotropic agents that can be used during incubation with the at least one protein-degrading compound are chaotropic salts which include but are not limited to guanidinium hydrochloride, guanidinium thiocyanate, guanidinium isothiocyanate, sodium thiocyanate, sodium iodide, sodium perchlorate, sodium trichloroacetate, sodium trifluroacetate, urea and the like.

In step b) i, the stabilized body sample or portion, fraction of component obtained from the stabilized body sample is preferably contacted with all additives aa), bb) and cc) described above and the resulting lysis composition is incubated to provide a lysed sample. Preferably, incubation step is performed under heating. Preferably, the lysis composition comprising the proteolytic enzyme is heated at least to a temperature of 35° C., at least 40° C., or at least 50° C. and preferably is heated to a temperature of at least 55° C. during incubation. Using respective higher temperatures during incubation is in particularly favourable if a proteolytic enzyme such as proteinase K is used as protein-degrading compound that shows its optimal, respective highest activity at higher temperatures. Under such conditions, the digestion is promoted. Of course, a temperature should be used wherein the proteolytic enzyme is active. Furthermore, it is preferred that the said incubation step is performed while agitating the resuspended sample. Non-limiting examples of agitation include shaking, stirring, mixing, or vibrating. In certain aspects, agitation comprises shaking. The shaking can be one, two, or three dimensional shaking. A variety of shaking or agitating devices can be used. Non-limiting examples include the Thermomixer (Eppendorf), TurboMix (Scientific Industries), Mo Bio Vortex Adapter (Mo Bio Laboratories), Microtube holder vortex adapter (Troemner), and the Microtube foam rack vortex attachment (Scientific Industries). Agitating can be performed for example in a mixer with at least 50 rpm, at least 100 rpm, at least 200 rpm or at least 500 rpm. Preferably, heating and agitation is simultaneously performed, for example by using a thermomixer or an equivalent apparatus that allows simultaneous heating and agitation. When using at least one proteolytic enzyme, incubation conditions are used that ensure that said enzyme works efficiently and is catalytically active. The conditions depend on the proteolytic enzyme used and are known, respectively determinable by the skilled person. Preferably, the incubation is performed in the presence of salts and/or ions that promote and/or maintain the activity of the proteolytic enzyme. Suitable salts include but are not limited to NaCl, KCl, $MgCl_2$, or $CaCl_2$ or chaotropic agents such as chaotropic salts.

In step b) ii, nucleic acids are isolated from the lysed sample by binding them to a solid phase in the presence of at least one chaotropic salt and at least one alcohol.

As solid phase, any material that is capable of binding nucleic acids that are present in or are released from a sample can be used and include a variety of materials that are capable of binding nucleic acids under suitable conditions. Exemplary solid phases that can be used in conjunction with the present invention include, but are not limited to, compounds comprising silica, including but not limited to, silica particles, silicon dioxide, diatomaceous earth, glass, alkylsilica, aluminum silicate, and borosilicate; nitrocellulose; diazotized paper; hydroxyapatite (also referred to as hydroxyl apatite); nylon; metal oxides; zirconia; alumina; polymeric supports, diethylaminoethyl- and triethylaminoethyl-derivatized supports, hydrophobic chromatography resins (such as phenyl- or octyl Sepharose) and the like. The term solid phase is not intended to imply any limitation regarding its form or design. Thus, the term solid phase encompasses appropriate materials that are porous or non-porous; permeable or impermeable; including but not limited to membranes, filters, sheets, particles, magnetic particles, beads, gels, powders, fibers, and the like. According to one embodiment, the surface of the solid phase such as e.g. the silica solid phase is not modified and is, e.g., not modified with functional groups. According to a preferred embodiment, a solid phase comprising silica is used. Silica based nucleic acid isolation methods are broadly used in the prior art. The solid phase comprising silica may e.g. have the form of a filter, fibers, membrane or particles. Also feasible is the use of silica particles that can be used in form of beads and which preferably have a particle size of about 0.02 to 30 μm, more preferred 0.05 to 15 μm and most preferred of 0.1 to 10 μm. To ease the processing of the nucleic acid binding solid phase, preferably magnetic silica particles are used. The magnetic silica particles may e.g. be ferrimagnetic, ferromagnetic, paramagnetic or superparamagnetic. Suitable magnetic silica particles are for example described in WO 01/71732, WO 2004/003231 and WO 2003/004150. Other magnetic silica particles are also known from the prior art and are e.g. described in WO 98/31840, WO 98/31461, EP 1 260 595, WO 96/41811 and EP 0 343 934 and also include for example magnetic silica glass particles. Furthermore, a nucleic acid binding solid phase that is comprised in a column can be used. The term "column" as used herein in particular describes a container having at least two openings. Thereby, the binding mixture can pass through said column. The term "column" in particular does not imply any restrictions with respect to the shape of the container which can be e.g. round or angular and preferably is cylindrical. However, also other shapes can be used, in particular when using multi-columns. The column comprises the nucleic acid binding solid phase. Said solid phase that is comprised in said column should allow the passage of the binding mixture according to the present invention when applied to the column. The column can be used in a single format or in a multi-format. Such multi-columns having a similar format as multi-well plates and which comprise a nucleic acid binding solid phase such as a membrane, are well-known in the prior art. Preferably, the column is a spin column. As nucleic acid binding solid phase, any solid phase can be used that is usually utilized in column based nucleic acid isolation procedures. Preferably, the nucleic acids bind to the solid phase by adsorption. The material of the nucleic acid binding solid phase that is included in the column may as described above be made of or may comprise compounds comprising silicon dioxide including but not limited to silica, silica particles, silicon dioxide, diatomaceous earth, glass, alkylsilica, aluminum silicate, and borosilicate; nitrocellulose; diazotized paper; hydroxyapatite (also referred to as hydroxyl apatite); nylon; metal oxides; zirconia; alumina; polymeric materials, materials comprising nucleic acid binding functional groups (preferably anion exchange groups) and the like. The term solid phase is not intended to imply any limitation regarding its form or design as long as it can be comprised in a column. According to one embodiment, the surface of the solid phase such as e.g. the silica solid phase is not modified and is, e.g., not modified with functional groups. Preferably, a nucleic acid binding membrane, and thus a membrane that is capable of binding nucleic acids is used. Suitable membranes include but are not limited to hydrophilic membranes, hydrophobic membranes and membranes which bind nucleic acids via ion exchange. Examples include but are not limited to membranes comprising or consisting of silicon dioxide, silica membranes, glass fiber membranes, nylon membranes, cellulose membranes such as nitrocellulose membranes, modified cellulose membranes (e.g. acetyl- or hydroxy-), paper membranes, in particular modified papers. Preferably, the membrane is porous.

Furthermore, it is preferred to use a membrane comprising or consisting of silica. A further common nucleic acid binding solid phase comprised in a column is a fill of nucleic acid binding particles, such as metal oxide particles, in particular silica particles, or a layer of a nucleic acid binding material (e.g. a silica gel). E.g. the nucleic acid binding particles such as the silica particles can be arranged as a layer on an inert filter or membrane, thereby forming a nucleic acid binding solid phase.

The binding of the nucleic acids to the solid phase is performed in the presence of at least one chaotropic agent, preferably a chaotropic salt and in the presence of at least one alcohol. Also a mixture of chaotropic agents can be used. In a preferred embodiment, a chaotropic agent is already used as additive cc) during lysis and hence, is incorporated in the lysis mixture. To establish the binding conditions, an additional amount of the same or a different chaotropic agent can be added. The concentration of the chaotropic agent or mixture of chaotropic agents that are used during binding may lie in a range of 0.05M up to the saturation limit. Preferred concentration ranges lie, depending on the chaotropic agent used, within 0.1M to 7M, 0.5M to 6M, 1.0M to 5M and 1.5M to 4M. Suitable chaotropic agents are in particular chaotropic salts and include but are not limited to guanidinium hydrochloride, guanidinium thiocyanate, guanidinium isothiocyanate, sodium thiocyanate, sodium iodide, sodium perchlorate, sodium trichloroacetate, sodium trifluoroacetate, urea and the like and in particular preferred are guanidinium hydrochloride, guanidinium thiocyanate and guanidinium isothiocyanate.

As alcohol, it is preferred to use short chained branched or unbranched alcohols with preferably one to 5 carbon atoms. Examples are methanol, ethanol, propanol, isopropanol and butanol. Also mixtures of alcohol can be used. The alcohol is preferably selected from isopropanol and ethanol. Preferably, the method according to the present invention does not involve the use of phenol and/or chloroform. The alcohol may be comprised in the binding mixture in a concentration of 10% v/v to 90% v/v, in particular 15% v/v to 80% v/v, 20% to 80% v/v. For isolating nucleic acids which also comprises small nucleic acids, it is beneficial to use an alcohol concentration of ≥30% v/v, preferably ≥40% v/v to ≤90% v/v. Respective higher concentrations of alcohol improve the binding and thus the isolation of short nucleic acids (usually having a size of 500 nt or less), in particular small RNA species. These concentrations work particularly well if the chaotropic agent(s) is/are present in higher concentrations and when binding the nucleic acids to a silica surface.

To establish suitable binding conditions, a binding solution which comprises e.g. the alcohol and the chaotropic agent can be added to the lysed sample.

Optionally, one or more detergents can be present during binding to promote binding of the nucleic acid to the solid phase. Preferably, at least one ionic and/or at least one non-ionic detergent is added. Preferably, a non-ionic detergent is used in the binding mixture in a concentration of at least 5%. Said detergent can be comprised in the binding solution that is added to establish the binding conditions. Furthermore, it can be alternatively or additionally provided by the lysed sample, if, what is preferred, lysis involved the use of one or more detergents.

Furthermore, a buffer can be added to the lysed sample, respectively can be incorporated in the binding solution. Non-limited examples of buffers include but are not limited to biological buffers such as HEPES, MES, MOPS, TRIS, BIS-TRIS Propane and others. Preferably, a Tris buffer is used in the binding solution.

Therefore, according to one embodiment, the nucleic acid isolation comprises in step b) ii the addition of a binding solution which comprises at least one alcohol and/or at least one chaotropic agent and optionally a buffer, preferably Tris, in order to establish the binding conditions that allow to bind the nucleic acid that are comprised in the lysed sample to the solid phase. Optionally, the binding solution additionally comprises a detergent as is described above. However, the components can also be added separately to establish suitable binding conditions in the binding mixture.

According to one embodiment, one or more washing steps are performed in order to further purify the isolated nucleic acids. According to one embodiment, one or more washing steps are performed while the nucleic acid is bound to the solid phase. For this purpose common washing solutions may be used. According to one embodiment, the solution used for washing comprises at least one chaotropic agent and at least one alcohol. Chaotropic agents that can be used in the washing solutions include but are not limited to guanidinium hydrochloride, guanidinium thiocyanate, guanidinium isothiocyanate and sodium iodide. As alcohol, short chained branched or unbranched alcohols with preferably one to 5 carbon atoms can be used for washing, respectively in the washing solution. Examples are methanol, ethanol, propanol, isopropanol and butanol. Preferably, isopropanol and/or ethanol are used. Preferably, the washing solution comprises at least 50% alcohol and at least 1M chaotropic salt, preferably at least 2M chaotropic salt.

A further suitable washing solution which can be used alternatively or also in addition to the washing solutions described above comprises an alcohol and a biological buffer. Suitable alcohols and biological buffers are described above. Preferably, isopropanol or ethanol, most preferred ethanol is used for this second washing step. Preferably, ethanol is used in a concentration of at least 70% v/v, preferably at least 80% v/v. The biological buffer is preferably Tris at a pH of approx. 7 to 8.

In case it is desired to perform an elution step to elute the nucleic acids from the solid phase, elution can be performed for example with classical elution solutions such as water, elution buffers, in particular biological buffers such as Tris and preferably elution solutions are used that do not interfere with the intended downstream application. After elution, the eluate can be heat denatured. However, it is also within the scope of the present invention to release and thus elute the nucleic acids from the solid phase by other elution means such as e.g. heating.

The isolated viral nucleic acids can then be analyzed and/or processed in a further step using suitable assay and/or analytical methods. E.g. they can be modified, contacted with at least one enzyme, amplified, reverse transcribed, cloned, sequenced, contacted with a probe and/or be detected. Respective methods are well-known in the prior art and are commonly applied in the medical, diagnostic and/or prognostic field in order to analyse viral nucleic acids and in particular to determine the viral load. Thus, after viral nucleic acids were isolated, they can be analyzed to identify the presence, absence or severity of a disease and/or disease state. E.g. the isolated viral nucleic acids can be analysed in order to detect diagnostic and/or prognostic markers in many fields of application, including but not limited to infectious disease testing, disease monitoring or many other virus based diseases and, hence, are of diagnostic and/or prognostic relevance. Thus, according to a preferred embodiment in a further step the virus particles and/or viral nucleic acids are analyzed to identify, detect, screen for, monitor or exclude a disease or to determine the viral load in a sample.

As discussed above, the isolation method described herein may comprise a further step of nucleic acid analysis and/or processing. The analysis/further processing of the nucleic acids can be performed using any nucleic acid analysis/processing method including, but not limited to amplification technologies, polymerase chain reaction (PCR), isothermal amplification, reverse transcription polymerase chain reaction (RT-PCR), reverse transcription, quantitative real time polymerase chain reaction (Q-PCR), digital PCR, gel electrophoresis, capillary electrophoresis, mass spectrometry, fluorescence detection, ultraviolet spectrometry, hybridization assays, DNA or RNA sequencing, restriction analysis, reverse transcription, NASBA, allele specific polymerase chain reaction, polymerase cycling assembly (PCA), asymmetric polymerase chain reaction, linear after the exponential polymerase chain reaction (LATE-PCR), helicase-dependent amplification (HDA), hot-start polymerase chain reaction, intersequence-specific polymerase chain reaction (ISSR), inverse polymerase chain reaction, ligation mediated polymerase chain reaction, methylation specific polymerase chain reaction (MSP), multiplex polymerase chain reaction, nested polymerase chain reaction, solid phase polymerase chain reaction, or any combination thereof. Respective technologies are well-known to the skilled person and thus, do not need further description here.

The present invention also pertains to a method for stabilizing viral particles in a body sample, preferably a body fluid such as blood, or in a sample obtained therefrom, comprising the step of contacting the sample with a stabilization composition comprising at least one formaldehyde releaser. Details with respect to the stabilization composition and the body sample were described above. It is referred to the above disclosure which also applies here. Preferably, the body sample is a body fluid and more preferred is selected from blood, plasma or serum. The stabilization composition of the present invention may also be incorporated into a body sample collection device, in particular a blood collection assembly, preferably an evacuated collection device. Thereby, the stabilization may occur during the sample collection. Such devices typically include a container having an open and a closed end. The container is preferably a blood collection tube. The container type also depends on the sample to be collected. Also disclosed is a viral particle containing stabilized body sample, preferably a stabilized blood sample, comprised in a sample collection device, preferably a blood collection tube. Details with respect to the stabilization were described above. It is referred to the above disclosure which also applies here.

Furthermore, the present invention pertains to a method for the identification, quantification or monitoring of a virus disease, comprising performing the isolation method according to the first aspect of the present invention, wherein the isolated virus particles and/or viral nucleic acids are analyzed for the presence, absence, or severity of a virus disease or for monitoring a virus disease, in particular for determining the viral load. Details with respect to said method were described above, it is referred to the above disclosure which also applies here.

This invention is not limited by the exemplary methods and materials disclosed herein, and any methods and materials similar or equivalent to those described herein can be used in the practice or testing of embodiments of this invention. Numeric ranges are inclusive of the numbers defining the range. The headings provided herein are not limitations of the various aspects or embodiments of this invention which can be read by reference to the specification as a whole.

The term "solution" as used herein in particular refers to a liquid composition, preferably an aqueous composition. It may be a homogenous mixture of only one phase but it is also within the scope of the present invention that a solution comprises solid additives such as e.g. precipitates.

According to one embodiment, subject matter described herein as comprising certain steps in the case of methods or as comprising certain ingredients in the case of compositions, solutions and/or buffers refers to subject matter consisting of the respective steps or ingredients. It is preferred to select and combine preferred embodiments described herein and the specific subject-matter arising from a respective combination of preferred embodiments also belongs to the present disclosure.

The present application claims priority of prior application EP 12 181 135 filed on Aug. 21, 2012 the entire disclosure of which is incorporated herein by reference.

EXAMPLES

It should be understood that these examples are for illustrative purpose only and are not to be construed as limiting this invention in any manner.

I. Materials and Methods

A test system was designed, wherein virus particle-containing body fluid samples, here whole blood samples, were incubated at 37° C. or at room temperature (RT) for up to 7 days. The sample stabilizing properties of the stabilization composition of the present disclosure were tested at different time points (see below). The samples were processed according to the following protocols, where applicable (for details, see also the specific examples in the results section):

1. Stabilization

Whole blood (10 ml) was collected in collection tubes containing the stabilization composition shown in table 1 as one example for the stabilization compositions according to the present disclosure:

TABLE 1

| Substance | percentage/ 10 ml sample |
| --- | --- |
| by weight diazolidinyl urea | 20-30% |
| by weight aurintricarboxylic acid | 0.5-2.5% |
| by weight sodium fluoride | 0.05-1.5% |
| by weight EDTA | 5-15% |
| by weight glyceraldehyde | 1-8% |

As reference controls, 10 ml whole blood was collected into BD Vacutainer® K2EDTA tubes. HCV (10^5 IU/ml), Parvo B19 (10^3 IU/ml) and PDV (1:10.000 diluted) viral particles were added to the collected blood samples to simulate different viral loads and virus types. The tubes were incubated for up to 7 days at 37° C. The sample comprising Parvo B19 virus was incubated at room temperature.

2. Isolation

On day 0, day 2 and day 7 for HCV and PDV and day 3 and 6 for Parvo 19, aliquots underwent following procedures:
   i. Centrifugation: blood sample for 15 min @ 3000 UpM; for Parvo B19 virus followed by the centrifugation of plasma for 10 min @ 16.000×g (4° C.)
   ii. Purification of nucleic acids from the obtained plasma samples using the QIAamp Circulating NA Kit (according to handbook). Here, up to 1 ml (10 ml for Parvo B19 virus sample) sample input was used (less sample filled up with PBS to 1 ml (10 ml for Parvo B19 virus sample)); the nucleic acids were eluted in 60 µl Buffer AVE After the isolation, eluates were stored at −20° C. until all samples (including the samples incubated for 7 days) were purified.

3. Detection

Afterwards viral nucleic acids were quantified by real-time PCR using the Quantitect Probe RT-PCR Kit (or the artus Parvo B19 PCR Kit for the isolation of Parvo B19 viral nucleic acid). The HCV/PDV duplex assay (real time PCR) was carried out according to the conditions shown in tables 2 and 3. For detecting HCV, primers and labeled probes (5' FAM-BHQ 3') were used which detect a sequence region in the 5' untranslated region of the HCV genome. For detecting PDV, primers and labelled (5' HEX-BHQ 3') probes were used that detect a sequence region in the H gene of the PDV genome.

Table 2 shows the reaction setup for the real time PCR reaction and table 3 shows the cycling conditions and the cycle numbers.

TABLE 2

| HCV/PDV | well |
| --- | --- |
| MMx QuantiTect | 25 |
| Primer HCV-TM 5' 100 µM | 0.2 |

TABLE 2-continued

| HCV/PDV | well |
| --- | --- |
| Primer HCV-TM 3' 100 µM | 0.2 |
| Probe HCV | 0.1 |
| QuantiTect RT Mix | 0.5 |
| Probe PDV 100 µM | 0.1 |
| for PDV 100 µM | 0.2 |
| rev PDV 100 µM | 0.2 |
| Rnase free water | 8.5 |
| MMx | 35 |

TABLE 3

| 50° C. | 30 min | |
| --- | --- | --- |
| 95° C. | 15 min | |
| 94° C. | 15 sec | 45 |
| 60° C. | 1 min | |

4. Results of the PDV Quantification by Real-time PCR

Figure 1:
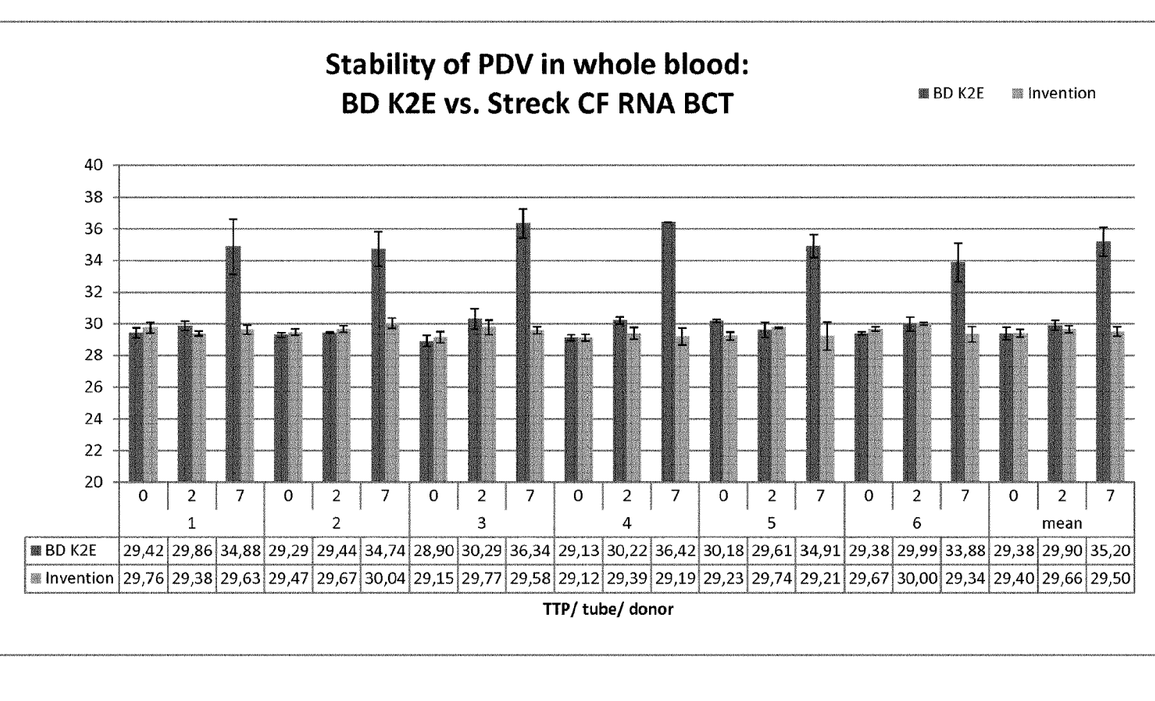
FIG. 1 is a diagram showing the effect of a stabilization composition according to the present disclosure on the stability of viral nucleic acids derived from the Phocine distemper virus (PDV).

FIG. 1 shows the effect of the stabilization composition shown in table 1 on the decrease of PDV nucleic acid levels in whole blood within 7 days of storage at 37° C. 6 different samples were analysed. The obtained Ct values are for each sample indicated at day 0, 2 and 7.

After 2 days, incubations of PDV at 37° C. shows no significant changes neither in EDTA reference control nor in the samples stabilized with the stabilization composition according to table 1 which comprises a formaldehyde releaser. But after 7 days of storage, the PDV CT values increases up to 5 cycles (equivalent to 32 fold decrease in viral load) in EDTA samples whereas remaining stable in the samples that use the stabilization composition according to the invention. Thus, in the EDTA stabilized samples, virus particles and in particular viral nucleic acids were severely degraded. Thus, using a stabilization composition comprising a formaldehyde releaser (see table 1), achieves a significant stabilizing effect on PDV virus loads in whole blood during longer storage periods.

5. Results of HCV and Parvo B19 Virus Quantification

In order to test for the stability of human infecting viruses, HCV and Parvo B19, representing an RNA and DNA virus, were spiked into whole blood samples. Assuming that viral degradation follows simple first order kinetics, half-life of HCV and Parvo B19 were calculated from decay curve allowing for direct quantification of the effect of the stabilisation composition of example 1. HCV and Parvo B19 were isolated analogous to PDV and detected by real time PCR. For HCV and Parvo B19, a standard curve was carried along, allowing to determine IU/ml and accordingly allowing to determine the half-life.

Table 4 shows the calculated half-lifes of HCV and Parvo B19 virus particles, stabilized in EDTA and in samples containing the stabilisation composition of example 1.

TABLE 4

| | Half-life [d] | | | | | | | |
| --- | --- | --- | --- | --- | --- | --- | --- | --- |
| | HCV (incubation @37° C.) | | | | | | | Parvo B19 |
| | Donor | | | | | | | (@RT) |
| Collection | 1 | 2 | 3 | 4 | 5 | 6 | mean | mean |
| BD vacutainer K2E | 2 | 1 | 1 | 1 | 3 | 2 | 2 | 3 |

TABLE 4-continued

| | Half-life [d] | | | | | | | |
| --- | --- | --- | --- | --- | --- | --- | --- | --- |
| | HCV (incubation @37° C.) | | | | | | Parvo B19 | |
| | Donor | | | | | | (@RT) | |
| Collection | 1 | 2 | 3 | 4 | 5 | 6 | mean | mean |
| Formaldehyde releaser stabilisation | 6 | 1 | 5 | 4 | >7 | 5 | 5 | 5 |

Already within 2-3 days of storage half of the Parvo B19 and HCV particles were degraded in blood samples that were stabilized by EDTA. In contrast to that, in the blood samples that were stabilized with the stabilisation composition of example 1, a corresponding decrease in the viral loads was only detected after 4 or 5 days of storage and thus after significantly prolonged time. This demonstrates the remarkable stabilisation effect on virus particles and virus nucleic acids achieved with the formaldehyde releaser stabilisation composition that is used according to the present invention. For some samples/donors, the half-life of the stabilized viruses extended even beyond 5 days and even beyond 7 days. Considering a half-life of 7 days that can be achieved using a formaldehyde releaser based stabilization as described herein, this means that even after a month of storage, 1/16 of the virus particles would be present, allowing a secure detection for many applications. Furthermore, it is noted that the decrease in target detection that is observed after prolonged storage is also not necessarily attributable to a decrease in the comprised viral particles and/or viral nucleic acids. Rather, this decrease could also be attributable to that the isolation of the viral nucleic acids becomes impaired after prolonged storage due to the strong stabilization effects of the formaldehyde releaser which may lead to a tighter linkage of the nucleic acids to proteins over time, thereby disturbing the nucleic acid isolation after prolonged storage. Thus, even though the viral particles and viral nucleic acids are efficiently stabilised also during prolonged storage, the detection could decrease due to an impairment of the nucleic acid isolation. Improving the nucleic acid isolation from formaldehyde releaser stabilized samples could overcome the observed decrease in target detection. The results presented herein accordingly demonstrate the stabilizing effect by the stabilisation compositions according to the present disclosure on RNA and DNA viruses like HCV and Parvo B19. The virus particles and viral nucleic acids decrease substantially more slowly in samples containing a stabilisation composition of the disclosure than in EDTA stabilized samples, thereby allowing prolonged storage times.

The invention claimed is:

1. A method for isolating viral particles and/or viral nucleic acids from a biological sample obtained from a body, comprising the steps of:
   a) obtaining a stabilized body sample, wherein said sample contains viral particles and/or viral nucleic acids and was stabilized by contacting the body sample with a stabilization composition comprising at least one formaldehyde releaser agent to stabilize viral particles and viral nucleic acids comprised in the sample;
   b) isolating viral particles and/or viral nucleic acids from the stabilized sample or from a portion, fraction or component of the stabilized sample; and
   c) analyzing and/or detecting the isolated viral particles and/or viral nucleic acids.

2. The method according to claim 1, wherein the formaldehyde releaser agent has one or more of the following characteristics:
   the formaldehyde releaser agent is a chemical fixative;
   the formaldehyde releaser agent is selected from the group consisting of diazolidinyl urea, imidazolidinyl urea, dimethoylol-5,5dimethylhydantoin, dimethylol urea, 2-bromo-2-nitropropane-1,3-diol, oxazolidines, sodium hydroxymethyl glycinate, 5-hydroxymethoxymethyl-1-1 aza-3,7-dioxabicyclo [3.3.0] octane, 5-hydroxymethyl-1-1 aza-3,7dioxabicyclo [3.3.0]octane, 5-hydroxypoly[methyleneoxy]methyl-1-1 aza-3, 7dioxabicyclo[3.3.0]octane, quaternary adamantine and any combination thereof;
   the formaldehyde releaser agent is a heterocyclic urea;
   the formaldehyde releaser agent is selected from diazolidinyl urea and imidazolidinyl urea; and/or
   the formaldehyde releaser agent is diazolidinyl urea.

3. The method according to claim 1, wherein the sample was stabilized additionally using one or more enzyme inhibitors or wherein the sample was stabilized using a stabilization composition additionally comprising one or more enzyme inhibitors, wherein said enzyme inhibitor has one or more of the following characteristics:
   the enzyme inhibitor is nuclease inhibitor;
   the enzyme inhibitor is selected from the group consisting of: dithiothreitol (DTT), iodoacetamide, iodoacetic acid, heparin, chitosan, cobalt chloride, diethyl pyrocarbonate, ethanol, aurintricarboxylic acid (ATA), glyceraldehydes, sodium fluoride, ethylenediamine tetraacetic acid (EDTA), formamtde, vanadyl-ribonucleoside complexes, macaloid, hydroxylamine-oxygen- cupric ion, bentonite, ammonium sulfate, beta-mercaptoethanol, cysteine, dithioerythritol, tris (2-carboxyethyl) phosphene hydrochloride, a divalent cation and any combination of the foregoing; and/or
   the enzyme inhibitor is aurintricarboxylic acid.

4. The method according to claim 1, wherein the sample was stabilized additionally using one or more metabolic inhibitors or wherein the sample was stabilized using a stabilization composition additionally comprising one or more metabolic inhibitors, the metabolic inhibitor having one or more of the following characteristics:
   i) the metabolic inhibitor is selected from the group consisting of: dihydroxyacetone phosphate, glyceraldehyde 3-phosphate, 1,3-bisphosphoglycerate, 3-phosphoglycerate, 2-phosphoglycerate, phosphoenolpyruvate, pyruvate and glycerate dihydroxyacetate, sodium fluoride, $K_2C_2O_4$ and any combination of the foregoing;
   ii) the metabolic inhibitor is glyceraldehyde;
   iii) the metabolic inhibitor is sodium fluoride; and/or
   iv) the metabolic inhibitor is a combination of glyceraldehyde and sodium fluoride.

5. The method according to claim 1, wherein the sample was stabilized additionally using one or more metal ion chelators or wherein the sample was stabilized using a stabilization composition additionally comprising one or more metal ion chelators, wherein the metal ion chelator is selected from the group consisting of ethylene glycol tetraacetic acid (EGTA), 1,2-bis-(o-Aminophenoxy)-ethane-N', N',N',N'-tetraacetic acid tetraacetoxy-Methyl ester (BAPTA-AM), dietyldithiocarbamate (DEDTC), ethylenediaminetetraacetic acid (EDTA), dicarboxymethyl- glutamic acid, nitrilotriacetic acid (NTA), ethylenediaminedisuccinic acid (EDDS), EDTA and any combination of the foregoing.

6. The method according to claim 1, wherein the stabilization composition comprises a formaldehyde releaser agent selected from a chemical fixative that contains urea and wherein for stabilization at least one or all of the following components was used or was comprised in the stabilization composition:
    an enzyme inhibitor;
    a metabolic inhibitor; and/or
    a metal ion chelator.

7. The method according to claim 6, wherein the stabilization composition has one or more of the following characteristics:
    it comprises a formaldehyde releaser agent between 20-30 percent by weight;
    b) it comprises an enzyme inhibitor between 0.5-2.5 percent by weight;
    c) it comprises a metabolic inhibitor between 0.05 and 8 percent by weight; and/or
    d) it comprises a metal ion chelator between 5-15 percent by weight.

8. The method according to claim 7, wherein the body sample has one or more of the following characteristics:
    it comprises viral particles;
    it is selected from the group consisting of body fluids, whole blood, blood products, plasma, serum, tissue, flexible tissue, bone marrow aspirates, lymphatic fluid, urine, liquor, ascites, milk, saliva, amniotic fluid, semen/seminal fluid, nasal secretions, nasal washings, bronchoalveolar lavages, vaginal secretions and wound secretions and excretions;
    it is a cell-free, cell-depleted or cell-containing fluid body sample;
    it is selected from whole blood, plasma, serum and/or bone marrow aspirates; and/or
    it is whole blood.

9. The method according to claim 1, comprising isolating the viral particles and/or viral nucleic acids from the obtained stabilized sample which is stored without refrigeration for a time period selected from
    a) at least two days;
    b) at least three days;
    c) at least one day to at least three days;
    d) at least one day to at least six days; and/or
    e) at least one day to at least seven days.

10. The method according to claim 1, comprising one or more of the following steps:
    contacting the sample with the stabilization composition directly after and/or during the collection of the sample;
    subjecting the stabilized sample to a nucleic acid analysis and/or detection method;
    isolating viral particles from the stabilized sample and analyzing or detecting the particles and/or isolating nucleic acids from said viral particles;
    isolating viral nucleic acids from the stabilized sample or from a portion, fraction or component thereof and analyzing and/or detecting the isolated nucleic acids;
    removing cells comprised in a cell-containing stabilized sample prior to performing an isolation, analysis and/or detection step; and/or
    performing a viral nucleic acid isolation step after a period of at least two days.

11. The method according to claim 1, comprising one or more of the following steps:
    i) removing cells from a cell-containing body sample between step a) and step b) according to claim 1;
    ii) storing the stabilized sample;
    iii) isolating viral particles from the stabilized sample or a portion, fraction or component thereof by binding them to a solid phase;
    iv) isolating viral nucleic acids in step b) using an isolation method selected from the group comprising extraction, solid-phase extraction, isolation methods using a nucleic acid binding solid phase, isolation methods using a silica material, isolation methods that are based on the use of a solid phase comprising anionic exchange groups; magnetic particle-based purification, alcohol and/or chaotropic agent(s) based nucleic isolation method, chromatography, anion-exchange chromatography, anion exchange particle-based isolation, electrophoresis, filtration, precipitation, target nucleic acid specific isolation methods and combinations thereof.

12. The method according to claim 1, wherein step b) comprises:
    lysing the stabilized body sample or lysing a portion, fraction of component obtained from the stabilized body sample thereby providing a lysed sample;
    providing a binding composition comprising the lysed sample, at least one chaotropic salt and at least one alcohol and binding nucleic acids comprised in the binding composition to a solid phase;
    optionally washing bound nucleic acids;
    optionally eluting bound nucleic acids.

13. The method according to claim 12, wherein step b) i. comprising contacting the sample with one or more, or all of the following lysing agents:
    aa) a proteolytic enzyme;
    bb) one or more detergents;
    cc) at least one chaotropic agent.

14. A method for stabilizing viral particles in a biological sample obtained from a body or in a sample derived therefrom, comprising the step of contacting the sample with a stabilization composition comprising at least one formaldehyde releaser agent, wherein the sample contains viral particles.

15. The method of claim 1, wherein the method is for determining the presence, absence, or severity of a viral disease or for monitoring and/or for determining the viral load.

16. The method according to claim 6, wherein the enzyme inhibitor is aurintricarboxylic acid, the metabolic inhibitor is glyceraldehyde and/or sodium fluoride, and/or the metal ion chelator is EDTA.

17. The method according to claim 7, wherein the metabolic inhibitor is glyceraldehyde between 1-8 percent by weight and/or sodium fluoride between 0.05-1.5 percent by weight.

18. The method according to claim 13, wherein the sample is contacted for lysis with at least one non-ionic detergent and/or at least one ionic detergent.

* * * * *

UNITED STATES PATENT AND TRADEMARK OFFICE
CERTIFICATE OF CORRECTION

PATENT NO. : 10,233,508 B2
APPLICATION NO. : 14/422979
DATED : March 19, 2019
INVENTOR(S) : Martin Horlitz et al.

It is certified that error appears in the above-identified patent and that said Letters Patent is hereby corrected as shown below:

In the Claims

Column 28, Claim 14:
Cancel the text beginning with "14. A method for stabilizing" to and ending with "viral particles."
Insert the following claim:
--14. A method for stabilizing viral particles in a biological sample obtained from a body or in a sample derived therefrom, comprising the step of contacting the sample with a stabilization composition comprising at least one formaldehyde releaser agent, wherein the sample contains viral particles, wherein the stabilization composition has one or more of the characteristics:
    1) the stabilization composition further comprises at least one or all of the following components:
        a) an enzyme inhibitor,
        b) a metabolic inhibitor, and/or
        c) a metal ion chelator,
    2) it comprises the formaldehyde releaser agent between 20 – 30 percent by weight;
    3) it further comprises an enzyme inhibitor between 0.5-2.5 percent by weight;
    4) it further comprises a metabolic inhibitor between 0.05 and 8 percent by weight; and/or
    5) it further comprises a metal ion chelator between 5-15 vol. percent by weight.--

Signed and Sealed this
Twenty-second Day of October, 2019

Andrei Iancu
*Director of the United States Patent and Trademark Office*